United States Patent [19]

Alleman

[11] 4,162,145
[45] Jul. 24, 1979

[54] REGENERATION OF LIQUID ABSORBENTS

[75] Inventor: Carl E. Alleman, Bartlesville, Okla.

[73] Assignee: Phillips Petroleum Company, Bartlesville, Okla.

[21] Appl. No.: 858,935

[22] Filed: Dec. 9, 1977

[51] Int. Cl.² .................. B01D 53/14; C07C 29/26
[52] U.S. Cl. .................................... 55/32; 55/89;
203/18; 203/23; 203/42; 203/71; 203/88;
260/450
[58] Field of Search .................. 203/18, 68, 69, 70,
203/52, 88, 42, 84, 71, 23; 568/868, 871; 55/32,
89; 260/450

[56] References Cited

U.S. PATENT DOCUMENTS

| | | | |
|---|---|---|---|
| 2,228,431 | 1/1941 | Archibald et al. | 203/52 |
| 3,105,748 | 10/1963 | Stahl | 203/18 |
| 3,321,890 | 5/1967 | Barnhart | 55/32 |
| 3,349,544 | 10/1967 | Arnold et al. | 55/32 |
| 3,471,370 | 10/1969 | Jubin | 203/68 |
| 3,531,449 | 9/1970 | Alvarez et al. | 203/18 |
| 3,690,816 | 9/1972 | Alleman | 423/228 |
| 3,736,725 | 6/1973 | Alleman et al. | 55/32 |

*Primary Examiner*—Wilbur L. Bascomb, Jr.

[57] ABSTRACT

A method for separating two liquid components from a mixture by distilling the mixture in the presence of a third liquid which is immiscible at least with the component having the higher boiling point with the third liquid having a boiling range from at least the boiling point of the lower boiling component up to the boiling point of the higher boiling component. In a preferred embodiment the liquid mixture components are glycol and water and the third liquid is a naphtha fraction having a boiling range from about 212° F. (100° C.) to about 410° F. (210° C.).

10 Claims, 1 Drawing Figure

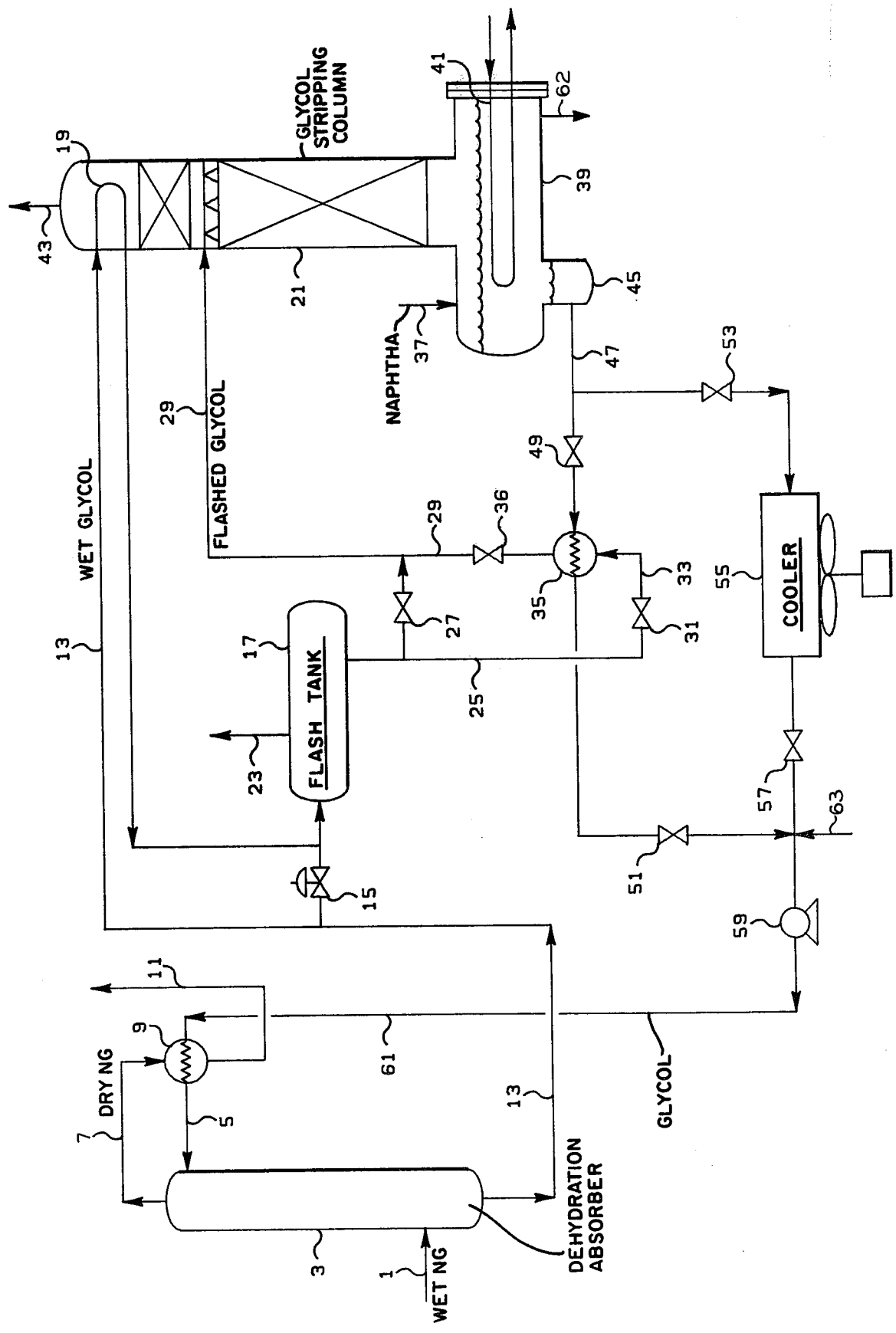

REGENERATION OF LIQUID ABSORBENTS

BACKGROUND OF THE INVENTION

This invention relates to liquid separation. In one of its aspects this invention relates to the distillation of a liquid mixture. In another of its aspects this invention relates to the stripping of a liquid from a two component mixture using a third liquid as stripping, refluxing, and heat transfer medium. In another of its aspects this invention relates to the regeneration of a glycol dehydrating agent. In still another aspect of the invention it relates to a process for removing water from natural gas using a glycol desiccant.

To avoid condensation or hydrate formation during pipeline transmission or during gas processing of natural gas, it is the usual process to remove water from the natural gas. One of the most widely used methods for removing water from natural gas is absorption with a glycol. Glycol absorption systems are, however, subject to such problems as (1) wasteful use of stripping gas in the process of regenerating glycol by the removal of water, (2) high energy requirements in applicable processes for removing water from the glycol, (3) disposal of water removed in the stripping process, and (4) generally poor stripping efficiency.

It is therefore an object of this invention to provide a method for regenerating glycol by stripping water therefrom which has both improved stripping efficiency and lower energy requirements than processes prevalent in the art. It is also an object of this invention to provide a system for regenerating glycol that conserves the use of stripping gas. It is another object of this invention to provide a method for stripping water from a glycol which results in easy disposal of the water removed. it is also an object of this invention to provide a general method for separating two liquid components from a mixture thereof using a third liquid which is essentially immiscible with at least one of the components of the mixture as a stripping, refluxing, and heat transfer medium.

Other aspects, objects, and the various advantages of this invention will become apparent upon reading the specification, studying the drawing, and reading the appended claims.

STATEMENT OF THE INVENTION

This invention provides a method for separating two liquid components from a mixture thereof in which the mixture is distilled in the presence of a third liquid which is essentially immiscible with, at least, the component of the mixture having the higher boiling point with the third liquid having a boiling range from at least that of the lower boiling component up to the boiling point of the higher boiling component. The third liquid acts as a stripping agent, a refluxing agent, and a heat transfer medium throughout the distillation process that removes the lower boiling component from the higher boiling component of the mixture.

In an embodiment of the invention a charge of naphtha is introduced into a triethylene glycol distillation column in which water is being removed from the glycol. The naphtha has a boiling range of about 212° F. (100° C.) to about 410° F. (210° C.) which encompasses the desired condensing temperature of the process and slightly exceeds the reboiling temperature of the process so that the naphtha serves both as a heat transfer and a stripping agent. In the process, the naphtha charge remains captive in the distillation column, being distributed throughout the column with the lighter fractions in the upper part of the column and the heaviest fraction remaining as a boiling pool in the distillation column reboiler. The various naphtha fractions are continuously vaporized and condensed throughout the column supplying the stripping action for removing water from the wet glycol and supplying reflux action which prevents glycol from being lost overhead.

In one preferred embodiment of the invention the condensing temperature of the distillation process is maintained at or near the boiling point of water so that the water stripped from the mixture is yielded from the column as a vapor. In this mode of operation the reflux in the column is primarily a condensed naphtha fraction containing a minor amount of water. This operation provides advantages which include elimination of the disposal of liquid water, minimizing the amount of liquid water in the rectification portion of the column thereby improving its separation effectiveness, and eliminating the revaporizing of water product thereby reducing the energy requirements of the system.

In another preferred embodiment, a sufficient amount of the heavier naphtha fractions is retained in the reboiler portion of the column to submerge the entire reboiler heat exchange bundle in a liquid naphtha phase. This improves the heat transfer in the system since it allows the entire reboiling heat requirement to be transmitted to boiling naphtha rather than boiling glycol. The naphtha has a much lower viscosity which can result in film boiling heat transfer coefficients more than five times greater than those obtained with glycols. The heat stability of the naphtha as compared to the glycol makes it possible to supply heat to the reboiler using hotter heat transfer fluids. The combination of higher heat transfer coefficients and greater Δt makes it possible to greatly reduce the size of the reboiler heat exchange bundle. As a corollary benefit the glycol is not degraded by exposure to film temperatures high enough to affect its stability.

Triethylene glycol decomposes significantly above 400° F. (204° C.). Also, in the case of hot-oil or steam heating medium, it is difficult to get temperatures above about 500° F. (260° C.); therefore, the naphtha temperature must be kept down toward 400° F. (204° C.) in order to maximize the thermal driving force and minimize the amount of heat transfer area required. Ethylene glycol and diethylene glycol decompose significatly at 328° F. (165° C.).

One of the advantages of the stripping system of this invention is improved energy efficiency. This invention provides up to about 40 cu. ft. of stripping gas per gallon of glycol, yet the energy input required is only that needed to desorb and vaporize the water plus what is required to raise the glycol temperature from feed temperature to reboiler temperature. The heat demand for raising the glycol temperature can be substantially reduced by indirect heat exchange of the hot regenerator glycol with the cold, wet desiccant being fed to the stripping column. This technique is common practice as is shown in U.S. Pat. No. 3,690,816. Economic considerations dictate the degree to which this heat exchange can be carried out. It has been found by calculation that even if this exchange is carried out to the extreme of a 10° F. (5.5° C.) approach, the remaining heat requirement is still sufficient to generate on the order of 9 cu. ft. of naphtha vapor per gallon of glycol regenerated.

This quantity of stripping gas is much greater than what is considered economical in other systems.

Another advantage of the present system is that no external stripping gas is required; therefore, none is wasted. It has been found in the past that where external gas has been supplied for stripping the gas rate has generally been limited to about 3 cu. ft. per gallon to avoid excessive waste of gas, but in the practice of this invention in a system such as one in which a glycol is used to absorb water from a wet natural gas with subsequent stripping of the water from the glycol so that the glycol can be recycled to the absorber, there will be no shortage of stripping vapor.

It should be noted that the invention is applicable to the stripping of any glycol absorbent, e.g., the various ethylene glycols, propylene glycols and the like, or any other absorbent that is not a solvent for naphthas. Mixtures of these absorbents can also be treated by the process of this invention.

The invention can best be understood in conjunction with the drawing which is a line diagram of a natural gas drying system using triethylene glycol desiccant with regeneration and recycle of the desiccant.

Referring now to the drawing, natural gas saturated with water at 80° F. (27° C.) and about 600 psia (4.14 MPa) and containing about 50 pounds of water per million standard cubic feet (MMSCF) is fed through line 1 to a dehydration absorber 3 to which is also fed through line 5 cooled triethylene glycol (TEG) desiccant. Dried natural gas leaves the absorber through line 7, passes in indirect heat exchange with inlet desiccant in heat exchanger 9, and is removed as product from the dehydrator system through line 11.

A controlled amount of wet glycol from the absorber at about 80° F. (27° C.) is passed through line 13 into the reflux condenser 19 located in the top of the glycol stripping column 21 to maintain the top of the stripping column at 212° F. (100° C.) thereby assuring that stripped water issues with the vented gases in the vapor phase. The remainder of the wet glycol from the absorber passes through control valve 15 to flash tank 17 where it is flashed at 50 psia (0.34 MPa). Flashed gases from the flash tank 17 pass through line 23 to fuel gas or other uses. If disposal of liquid water, contaminated with trace amounts of glycol, poses no problem, more heat can be conserved by condensing all the water. The liquid water is separated by gravity from condensed naphtha. Water is discarded and naphtha is passed back into the top of the column.

The flashed glycol from flash tank 17 passes through line 25 either directly through valve 27 and line 29 into the stripping column 21 or can be passed through valve 31 and line 33 into heat exchanger 35 to be indirectly heat exchanged with hot glycol from the reboiler settling leg before passing through valve 36 and line 29 into the stripping column 21. The latter alternative conserves more heat.

In the stripping column, naphtha with a boiling range of about 212° F. to about 410° F. (100°–210° C.) is charged through line 37 to the reboiler 39 with the glycol stripper in sufficient quantity to assure good coverage of the reboiler heat exchange bundle 41 during operation. The heating medium for the reboiler heat exchange bundle is hot oil maintained at an inlet temperature of 500° F. (260° C.) that is circulated to maintain the temperature at the bottom of the stripping column at 400° F. (204° C.). The top of the stripping column at condenser 19 is at essentially atmospheric pressure and is maintained by the condenser at about 212° F. (100° C.). It can be readily seen that any naphtha having a boiling point below 212° F. (100° C.) would be removed through vent line 43 along with vaporized water. The captive naphtha in the stripping column is, therefore, within the boiling range that has as its lower limit the temperature at which the top of the stripping column is maintained.

Hot glycol from the reboiler settling leg 45 passes through line 47 and can either be directed through valve 49, heat exchanger 35, and valve 51 or through valve 53, external cooler 55, and valve 57 to transfer means 59 with a reduction of temperature of the regenerated glycol to about 250° F. (121° C.) before it is transferred through line 61 and further cooled in heat exchanger 9 by heat transfer with the dry gas effluent from the dehydration absorber 3. As temperature of naphtha pool in reboiler 39 gradually increases, some can be withdrawn (through line 62) and fresh naphtha added (through 37) to keep the pool temperature within bounds. In lieu of using the dry gas effluent, another heat exchange medium can be used or another device for cooling can be used. Fresh glycol for the system can be supplied through line 63 at the suction of transfer means 59.

I claim:

1. A method for separating a water component and a glycol component from a liquid mixture thereof said method comprising distilling said liquids in the presence of a liquid naphtha fraction having a boiling range from at least that of the lower boiling component up to the boiling point of the higher boiling component.

2. A method of claim 1 wherein the glycol is triethylene glycol and the naphtha fraction has a boiling range from about 212° F. (100° C.) to about 410° F. (210° C.).

3. A process of claim 1 for regeneration of a glycol desiccant by removing water from mixture with the desiccant in a stripping column, said process comprising:
   (a) heat exchanging indirectly the stripping column overhead stream to maintain the overhead vapor leaving the stripping column at about 212° F. (100° C.),
   (b) introducing heat exchanged dessiccant into the stripping column at a point in the column below said heat exchanging,
   (c) maintaining in the stripping column a naphtha fraction having a boiling range from at least 212° F. (100° C.) to the boiling point of the glycol desiccant in an amount sufficient to provide the heat of vaporization necessary to regenerate the desiccant,
   (d) supplying, indirectly in a reboiling section of said column, heat sufficient to provide the required heat of vaporization to said naphtha fraction,
   (e) recovering vaporized water overhead, and
   (f) recovering desiccated glycol from said reboiler.

4. A process of claim 3 wherein said glycol is triethylene glycol and the temperature of said reboiler is maintained at about 410° F. (210° C.).

5. A process for removing water from natural gas comprising:
   (a) absorbing water from said natural gas with a glycol desiccant and
   (b) regenerating said glycol desiccant by the process of claim 3.

6. A process of claim 5 wherein wet liquid desiccant is flashed to remove entrained natural gas before being fed to said stripping column.

7. A process of claim 6 wherein desiccant recovered from the reboiler is recycled to the absorber.

8. A process of claim 7 wherein said recycled desiccant is cooled before recycle to the absorber.

9. A process of claim 8 wherein the recycled desiccant is cooled by indirect heat exchange with flashed, wet desiccant feet to the stripping column.

10. A process of claim 3 wherein the overhead stream is heat exchanged indirectly with wet glycol desiccant to maintain the overhead vapor leaving the stripping column at about 212° F. (100° C.).

* * * * *

UNITED STATES PATENT AND TRADEMARK OFFICE
CERTIFICATE OF CORRECTION

PATENT NO. : 4,162,145
DATED : July 24, 1979
INVENTOR(S) : Carl E. Alleman

It is certified that error appears in the above—identified patent and that said Letters Patent are hereby corrected as shown below:

Column 6, line 2, "feet" should be --- feed ---.

Signed and Sealed this

Sixth Day of November 1979

[SEAL]

Attest:

RUTH C. MASON
Attesting Officer

LUTRELLE F. PARKER
Acting Commissioner of Patents and Trademarks